United States Patent [19]

Burke et al.

[11] 4,433,687
[45] Feb. 28, 1984

[54] MICROSURGICAL SCISSORS

[75] Inventors: Roger M. Burke, Weston; Allen H. DeSatnick, Boston; George P. Honkanen, North Scituate, all of Mass.

[73] Assignee: Acufex Microsurgical, Inc., Norwood, Mass.

[21] Appl. No.: 362,400

[22] Filed: Mar. 26, 1982

Related U.S. Application Data

[63] Continuation of Ser. No. 146,100, May 2, 1980, abandoned.

[51] Int. Cl.$^3$ ............................................. A61B 17/32
[52] U.S. Cl. .................................. 128/318; 128/305; 30/240
[58] Field of Search ....................... 128/305, 318, 751; 30/240, 263

[56] References Cited

U.S. PATENT DOCUMENTS

| 1,493,240 | 5/1924 | Bohn | 128/305 |
| 3,921,640 | 11/1975 | Freeborn | 128/318 |
| 4,167,943 | 9/1979 | Banko | 128/305 |
| 4,258,716 | 3/1981 | Sutherland | 128/321 X |

FOREIGN PATENT DOCUMENTS

| 503439 | 6/1951 | Belgium | 128/305 |
| 2808911 | 3/1979 | Fed. Rep. of Germany | 128/305 |
| 2022421 | 12/1979 | United Kingdom | 128/751 |

Primary Examiner—Michael H. Thaler
Attorney, Agent, or Firm—Cesari and McKenna

[57] ABSTRACT

A microsurgical scissors uses a rotary cutting action and biased blades that intersect in a travelling point of contact. One blade is situated on the end of a tubular shaft and a second blade is on a rod that is rotatable within the shaft. The blades are angled so their cutting edges intersect each other. To assure a precise shearing relationship, the rod is biased rearward in order to bear the cutting edge of the rod blade against the cutting edge of the shaft blade. An actuating mechanism in the handle translates linear finger motion into rotary motion of the rod. The blades cut cleanly and surely without imparting undue tissue trauma.

6 Claims, 6 Drawing Figures

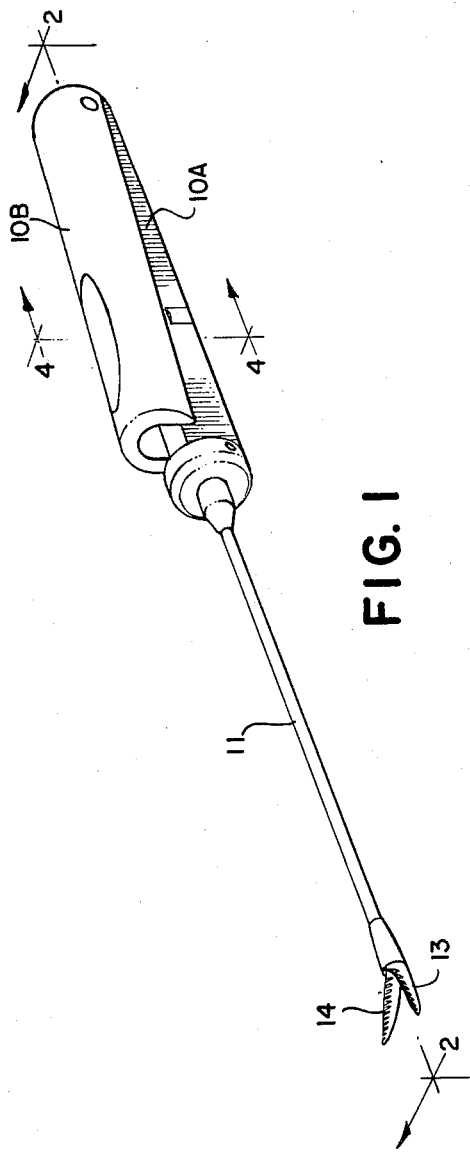
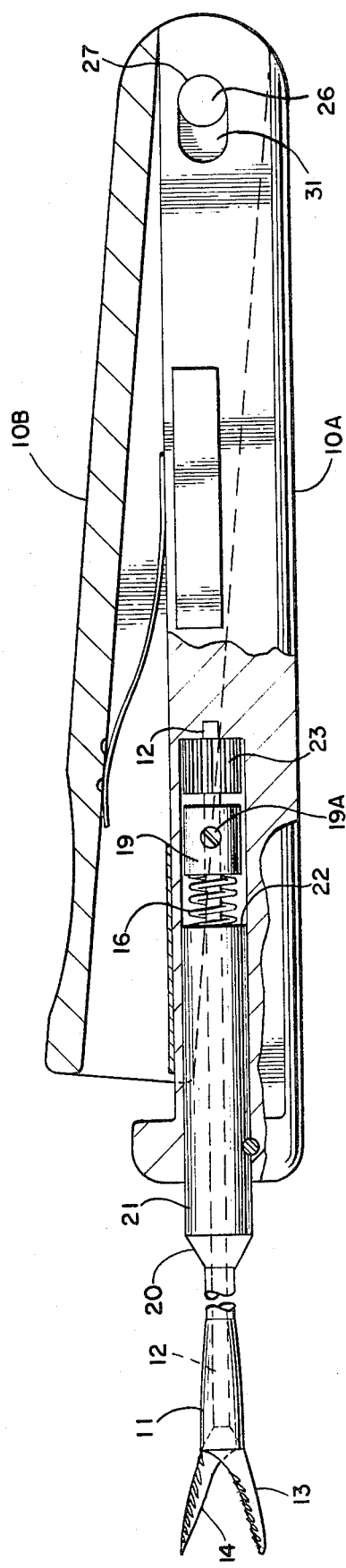

MICROSURGICAL SCISSORS

This is a continuation of application Ser. No. 146,100 filed May 2, 1980, now abandoned.

BACKGROUND OF THE INVENTION

This invention relates to microsurgical instruments for performing fine surgical tasks. More particularly, the invention relates to a microsurgical scissors with combined rotary action and axial biasing action for improving shearing action and durability.

Because successful microsurgery requires precision instrumentation for special surgical tasks, instrument designers and manufacturers face special problems. The microsurgical instrument must typically perform a delicate surgical task. Often it must be inserted into a small, relatively inaccessible area without itself causing trauma or displacing the position of tissues in the operating field. Because microsurgery demands the surgeon's concentrated attention, the surgical instrument must also operate simply and effectively to facilitate rather than complicate the surgeon's work. Moreover, the microsurgical instrument must not only perform its delicate operating task, but must also maintain its structural integrity. Because the instrument must be repeatedly used, its ability to maintain the proper relationship of its working parts helps to reduce hospital costs for replacing these expensive precision instruments.

One such instrument is a microsurgical scissors. The required characteristics of an ideal microsurgical scissors are illustrated by its use in arthroscopic surgery of the knee for repair of damaged meniscus pads. The operation typically uses the double-puncture technique in which two or more portals of entry (for example, anteromedial and anterolateral portals for repairing meniscus tears) allow arthroscopic viewing and dissection through one portal and retraction of loose or excised bodies through the second portal. Because this microsurgical procedure allows repair of the meniscus by a precision instrument as opposed to requiring partial or total removal as in arthrotomy, traumatic effects can be avoided.

Specifically, the size of the more conventional surgical instruments, the size of the incision, and the displacement of knee tissues necessary to reach the operating site often cause severe trauma to the patient, indeed much more severe than the trauma occasioned by meniscus repair itself. Moreover, the recovery period of an arthrotomy is measured in weeks and months, and the affected muscles, bones and skin may exhibit quadriceps inhibition, patellofemoral imbalance and painful scars, respectively.

Microsurgical procedures have been developed to redress these problems. The procedures use instruments that can reach the site of the operation through small incisions and with minimal displacement of intervening tissues. The working parts of one of these instruments, e.g. the blades of a scissors, are small and are positioned on the forward end of a narrow shaft that extends through a small portal of entry from the exterior. At the rearward end of the shaft are the control elements of the instrument, e.g. the handles of a scissors, which connect with the working parts through a linking rod within or adjacent to the shaft. Thus, the surgeon, by manipulating the control elements at a position external to the body, can perform a procedure at a remote operating site with minimal trauma to the patient.

In arthroscopic surgery, the working elements of the microsurgical scissors must be approximately 3-5 millimeters in diameter to be inserted through a small operating portal of entry. For successful surgery, the scissors must cut surely and precisely. To do so, the scissors must require only a small hand movement by the surgeon and must translate that movement to the shearing blades without altering their position in the operating field. In response, the faces of the blades must cooperate to cleanly shear, rather than tear, the meniscus.

To be practical, the microsurgical scissors must also endure post-operative cleaning, sterilizing and storing without sustaining debilitating damage. This lessens the expense of replacing the instrument and contributes to the success of the surgery by eliminating damaged instruments that complicate the surgeon's task. Particularly, the blades must continue to cooperate in their original, precise shearing relationship.

Prior microsurgical scissors have presented problems to surgeons. A number of instruments are illustrated by Rand in "Microneurosurgical Instrumentation," *Microneurosurgery* (1978); and by O'Connor, "Arthroscopic Surgery of the Knee," *Arthroscopy and Arthrography of the Knee* (1978). Other instruments are shown by White et al. (U.S. Pat. No. 3,834,021), Wallace (U.S. Pat. No. 2,691,370), and Stevenson (U.S. Pat. No. 1,754,806). These references all show a fixed blade on a forward extending shaft and a moving blade on a linking rod that moves axially with respect to the shaft. In each instrument, axial movement of the rod causes the blade attached to it to pivot in a shearing relationship with the fixed blade. Contact between the blades is maintained by tightly fastening the blades at the pivot point.

However, prior instruments suffer from a number of deficiencies, including misalignment or "play" in the blades. Significant surgical use and wear from cleaning, sterilizing and storing procedures causes such play at the pivot point. In turn, this play prevents the blades from bearing against each other at the traveling point of contact. Obviously, if the blades do not properly meet, they cannot cleanly shear; instead, they tend to tear the tissue.

With instruments like typical sewing scissors without a forward extending shaft and rod, the surgeon himself forces the blades to bear against each other at the point of contact by applying lateral pressure to the finger and thumb receiving grips of the handle. This is especially undesirable because it affects the surgeon's control required to make the cut and causes lateral movement of the blades with respect to the tissue.

Moreover, even the Wallace and Stevenson-type handle can displace the blades from the desired shearing area, since closing together the two members of the handle tends to vertically rotate the shaft, and hence the blades, of the instrument.

Further, prior art microsurgical scissors sometimes disassemble during an operation. If the pivot pin disengages from its position, the pin or a blade can fall from the instrument into the operating area, necessitating an independent recovery procedure.

Care of any microsurgical instrument is another major concern. Prior scissors, for example, can be easily bent or misaligned from mishandling during cleaning, sterilizing, and storing. Such damage can completely disable the instrument and contributes to the play or vertical displacement of the blades described above.

SUMMARY

Therefore, the principal object of this invention is a microsurgical instrument that will perform fine surgical tasks and withstand wear and damage. A further object is to provide a clean, sure, and precise shearing microsurgical scissors that can be inserted into a relatively small field of operation without undue tissue trauma or disruption. Another object is to provide such a microsurgical scissors that maintains its structural integrity and sustains minimal injury from mishandling.

This invention achieves the above and further objects in a microsurgical instrument that uses rotary motion of a rod within a shaft for rotating a working part on the forward end of the rod into a functioning relationship with a working part on the forward end of the shaft. The invention also provides locking means associated with the handle of the instrument for maintaining the element on the forward end of the rod and shaft in a closed position. A microsurgical scissors according to this invention uses rotary motion of a rod within a shaft for rotating a blade on the rod past a blade on the shaft in a shearing relationship, and also uses rearward tension of the rod with respect to the shaft for bearing the rod blade against the shaft blade as the rod blade rotates past in a shearing relationship. The rotatable rod lies within the tubular shaft, the rod and shaft each having a blade on its forward end. Actuating means associated with the handle rotates the rod, and thereby rotates the rod blade past the shaft blade. Further, the rod blade is angled with respect to the shaft blade so that the blades intersect at at least one point of contact when the rod blade passes the shaft blade in a shearing relationship. Biasing means continuously bears the rod blade against the shaft blade at the point of contact as the rotating rod blade causes the point of contact to travel.

The appended claims particularly point out the subject matter that the inventors regard as their invention. The following description and accompanying drawings set out the invention with particularity and show how the above and further objects are accomplished by the invention.

BRIEF DESCRIPTION OF THE DRAWING

FIG. 1 is a pictorial view of a microsurgical scissors with the blades in an open position.

FIG. 2 is a fragmentary side view with a partial cutout showing the relationship of certain parts within the handle.

DETAILED DESCRIPTION OF THE INVENTION

Figure 4:
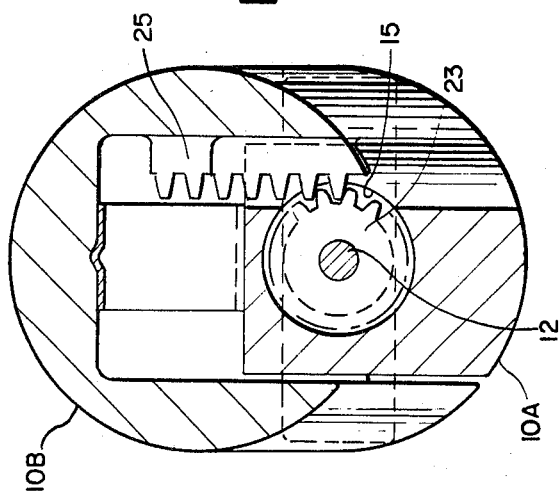
FIG. 4 is a section through the handle in the open position showing the actuating means.

FIG. 1 illustrates an exemplary microsurgical scissors that incorporates this invention. It includes a handle 10 for gripping the instrument, a tubular shaft 11 that extends forward from the handle, rod, a shaft blade 13 affixed to the forward end of the shaft 11 and a rod blade 14 affixed to the forward end of a rod 12 (not visible in FIG. 1) disposed within the shaft 11.

To actuate the scissors, the user compresses a slotted sleeve 10B in the handle 10 against a base 10A. This imparts a rotary motion to the rod 12, thereby moving the rod blade 14 in an arcuate path past the shaft blade 13. This relative movement of the two blades provides the shearing action of the scissors.

With reference to FIGS. 2 and 4, handle 10 includes substantially rectangular base 10A and sleeve 10B that fits over and accommodates base 10A. A tubular slot 15 runs longitudinally and substantially centrally through base 10A for accommodating the rearward extension of shaft 11 and rod 12.

The rearward extension of the shaft 11 and rod 12 that attach to the handle is depicted in FIG. 2. The rearward end 21 of the shaft is of greater diameter than the forward extending part of shaft 11 and has a rearward base 22. Rod 12 extends all the way through tubular shaft 11 and its rearward end 21.

At the rearward end of rod 12 is shown a biasing means that includes spring 16 and compressing element 19. Spring 16 encircles the rearward end of rod 12. Compressing means 19 is a nut-like element that forces spring 16 against the base 22 of the shaft. While the spring is in the compressed position, compressing means 19 is fastened into position, for example, by tightening a radially extending screw 19A that engages the rod. This produces rearward tension on the rod with respect to the shaft, and thereby causes blade 14 on the forward end of the rod to continuously bear against blade 13 on the forward end of the shaft.

Figure 3:
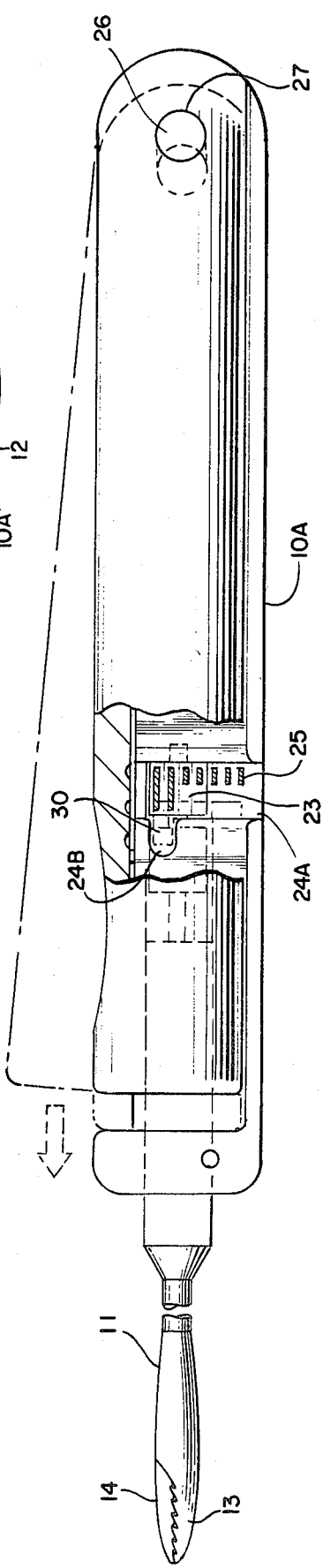
FIG. 3 is another side view showing the relationship of the rack and pinion in the closed positions.

Further, referring to FIGS. 2, 3 and 4, a pinion 23 is connected to the rod 12 such that rotary motion of the pinion 23 produces rotary motion of the rod 12, and arcuate motion of rod blade 14 with respect to shaft blade 13.

At the rearward end of the bore 15 is a side opening 24 in the base 10A that exposes the teeth of pinion 23. On the interior wall of sleeve 10B is a rack 25 (FIGS. 2 and 4) that engages the teeth of the pinion.

At the rearward end of the handle 10, base 10A and sleeve 10B are connected by a pivot pin 26 that frictionally fits within a hole 27 in the sleeve 10B and a slot 31 in the base 10A. When sleeve 10B is depressed, it pivots on pivot pin 26 from an open to a closed position and carries the rack 25 transversely with respect to the axis of rod 12. As it does, the teeth on the rack move into engagement with the teeth on pinion 23. The rod then rotates as sleeve 10B is further depressed to its complete closing position. As the rod rotates in response to actuation of the handle 10, the working element on the forward end of the rod, namely blade 14, rotates past stationary shaft blade 13.

With reference to a locking arrangement for the surgical instrument is shown in FIGS. 2 and 3. The opening 24 in base 10A is shaped like an inverted L with a vertical portion 24A and horizontal portion 24B.

When the sleeve 10B is in the closed position and rotary motion of the rod 12 is completed, forward movement of the sleeve is permitted by the slot 31 at the rearward end of base 10A. This forward movement moves a lug 30 at the upper end of pinion 23 into the horizontal portion 24B of opening 24 in the base 10A. This position of the lug 30 prevents vertical movement of the sleeve 10B and thus locks the rod 12 in the fully rotated position. As shown in FIG. 3, this retains the rod blade 14 in a fully closed, or rested position with respect to shaft blade 13.

Figure 5:
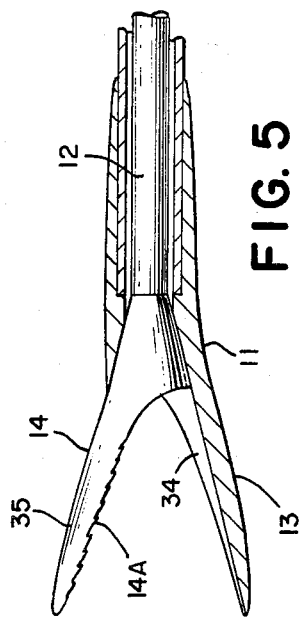
FIG. 5 is a view of the blades showing their relationship in the open position.

FIG. 5 shows the relationship of blades 13 and 14, the working elements on the forward ends of shaft 11 and rod 12, respectively. The shearing edges 13A and 14A of the blades are angled with respect to each other in the direction of relative movement of the blades, e.g. the circumferential direction. The angled edges intersect each other at a point of contact as viewed from the radial direction. As the rod blade 14 moves past the shaft blade 13, the point of contact moves from one end of the blades to the other.

Moreover, the blades make different angles with respect to the axis of the rod 12. Specifically, in the illustrated scissors, the rod blade 14 is tilted outward with respect to the axis to a greater extent than the shaft blade 13. Thus, the rearward pull on the rod 12 executed by the spring 16 (FIG. 2) causes the shearing edge 14A to bear against the edge 13A at the point of intersection. The scissors thus provides a highly efficient shearing action in response to rotation of the rod 12 by actuation of the handle 10.

Figure 6:
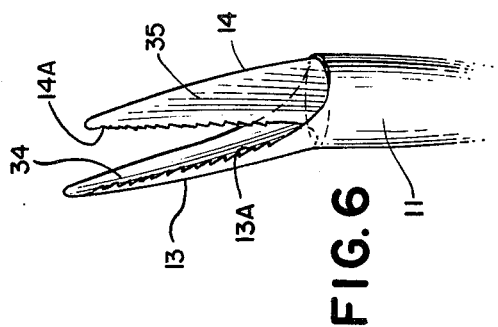
FIG. 6 is a view of the blades showing their conformation in a preferred embodiment.

FIGS. 5 and 6 further show that blades 13 and 14 are arcuate about the center of rotation of the rod. That is, the inner face 34 of shaft blade 13 and the outerface 35 of the rod blade 14 are formed to nest as the rod blade rotates through the shearing stroke. This facilitates non-interfering relative movement of the two blades.

In summary, we have provided a microsurgical instrument that performs precise surgical tasks and endures wear and handling. The drawings depict a particular configuration of working elements for a microsurgical scissors. However, this description is for purposes of explanation only. Various modifications of the specially described embodiment can be made while still achieving some or all of the benefits of this invention. For example, a microsurgical instrument such as a forceps could embody the same handle for gripping and actuating the instrument, the tubular shaft with a surgical gripping element on the forward end of the shaft, the rotatable rod with an opposing surgical gripping element on its forward end. Such a forceps might also include the locking means shown in FIGS. 2 and 4 for maintaining the gripping elements in closed relationship, as has been described. Therefore, we seek to cover in the appended claims all such variations and modifications that come within the true spirit and scope of his invention.

We claim:

1. In a microsurgical scissors comprising:
   a handle for gripping the scissors;
   a tubular shaft extending forward from the handle and having a blade on the forward end of the shaft;
   a rotatable rod within the shaft, the rod having a blade on its forward end for engaging the shaft blade, the rod blade and the shaft blade each having a cutting edge, the cutting edges being angled to intersect in a shearing relationship; and actuating means associated with the handle for rotating the rod, and thereby rotating the rod blade past the shaft blade in a shearing relationship so that the point of contact travels along the blades; the improvement wherein the blades are arcuate in form about the axis of the rod and shaft, said arcuate shape forming means for said blades to nest one in the other, and wherein the scissors comprise biasing means for urging the rod in a longitudinal direction with respect to the shaft, and thereby bearing the cutting edges of the rod and shaft blades against each other at a point of contact and wherein the cutting edges of the blades are angled with respect to each other in the circumferential direction of the rod, and tilted outward with respect to the axis of the rod and shaft.

2. The microsurgical scissors of claim 1, in which the biasing means includes a spring that encircles the rod and compressing means that cooperates with the spring for urging the inner shaft rearward.

3. The microsurgical scissors of claim 2, in which the actuating means includes means for coverting motion transverse to the axis of the rod into rotary motion of the rod.

4. The microsurgical scissors of claim 3, in which the converting means includes a rack associated with the handle, a pinion connected to the rearward end of the rod for engaging the rack, and driving means associated with the handle for moving the rack with respect to the pinion for rotating the rod.

5. The microsurgical scissors of claim 4, further comprising locking means associated with the handle for maintaining the inner shaft blade and outer shaft blade in a closed relationship.

6. The microsurgical scissors of claim 1, in which the cutting edge of the rod blade is tilted outward with respect to the axis of the rod and shaft to a greater extent than the cutting edge of the shaft blade.

* * * * *